United States Patent
Kheifetz et al.

(10) Patent No.: US 11,145,417 B2
(45) Date of Patent: Oct. 12, 2021

(54) METHOD AND SYSTEM FOR PREDICTION OF MEDICAL TREATMENT EFFECT

(71) Applicant: OPTIMATA LTD., Tel-Aviv (IL)

(72) Inventors: Yuri Kheifetz, Leipzig (DE); Yuri Kogan, Kiriat Ono (IL); Itamar Sela, Rehovot (IL); Zvia Agur, Tel-Aviv (IL)

(73) Assignee: OPTIMATA LTD.

(*) Notice: Subject to any disclaimer, the term of this patent is extended or adjusted under 35 U.S.C. 154(b) by 1049 days.

(21) Appl. No.: 15/116,202

(22) PCT Filed: Feb. 4, 2015

(86) PCT No.: PCT/IL2015/050123
§ 371 (c)(1),
(2) Date: Aug. 2, 2016

(87) PCT Pub. No.: WO2015/118529
PCT Pub. Date: Aug. 13, 2015

(65) Prior Publication Data
US 2017/0140109 A1 May 18, 2017

Related U.S. Application Data

(60) Provisional application No. 61/935,520, filed on Feb. 4, 2014.

(51) Int. Cl.
*G16H 50/50* (2018.01)
*G16H 50/20* (2018.01)
(Continued)

(52) U.S. Cl.
CPC .......... *G16H 50/50* (2018.01); *G16H 50/20* (2018.01); *G16H 20/10* (2018.01)

(58) Field of Classification Search
CPC ..... G06F 19/325; G06F 19/321; G16H 50/50; G16H 50/20
See application file for complete search history.

(56) References Cited

U.S. PATENT DOCUMENTS

| 6,108,635 A * | 8/2000 | Herren ............... G06Q 40/08 705/2 |
| 2004/0193019 A1 * | 9/2004 | Wei .................. A61K 31/519 600/300 |

(Continued)

FOREIGN PATENT DOCUMENTS

WO 02/32458 A2 4/2002

OTHER PUBLICATIONS

Office Action for Chinese Patent Application No. 201580007189.X dated Mar. 26, 2019 (English translation only).

(Continued)

*Primary Examiner* — Michael Tomaszewski
*Assistant Examiner* — Mohmad Muqueeth
(74) *Attorney, Agent, or Firm* — Dorsey & Whitney LLP

(57) ABSTRACT

A computerized system and method for planning a medical treatment for an individual under specific medical condition comprises a data input utility configured for receiving input data, and a data processor. The input data includes first input data comprising medical data of a specific individual, and second input data comprising data indicative of at least one endpoint of treatment. The data processor is configured for utilizing the medical data of the specific individual and the data indicative of the at least one endpoint and processing data indicative of disease progression models, each disease progression model corresponding to a treatment plan comprising one or more predetermined treatment protocols for treating the specific medical condition. The data processor generates output data indicative of a treatment effect on the individual with respect to each of the treatment plans and at least one endpoint to evaluate the treatment plans.

17 Claims, 4 Drawing Sheets

(51) Int. Cl.
*G16H 20/10* (2018.01)
*G06Q 50/00* (2012.01)

(56) References Cited

U.S. PATENT DOCUMENTS

| | | | |
|---|---|---|---|
| 2007/0156453 A1* | 7/2007 | Frielinghaus | A61N 5/103 |
| | | | 705/2 |
| 2011/0144518 A1 | 6/2011 | Causevic | |
| 2011/0144914 A1* | 6/2011 | Harrington | C12Q 1/6883 |
| | | | 702/19 |
| 2012/0029035 A1* | 2/2012 | Blight | A61K 31/4409 |
| | | | 514/352 |

OTHER PUBLICATIONS

Chin, J., The Clinical Side: Clinical trial endpoints—Pharmaceutical Representative, Aug. 2004.
Extended European Search Report, dated Dec. 1, 2017, for related EP Application No. 15746548.5.
International Search Report for PCT/IL2015/050123, dated Jun. 9, 2015.

* cited by examiner

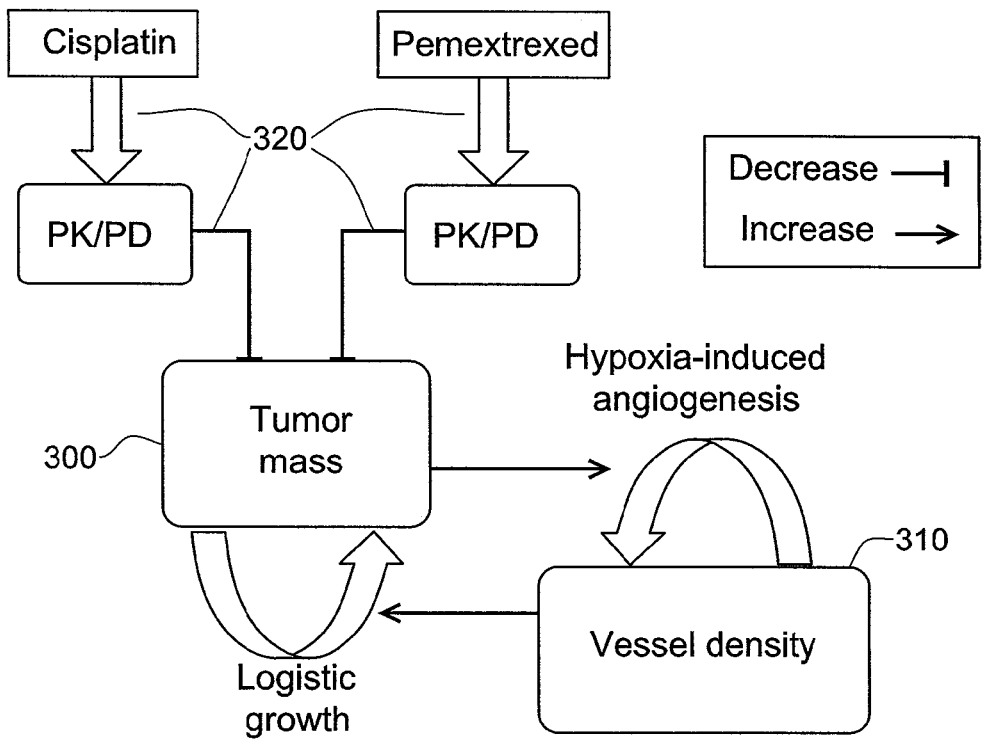

Fig. 4

$$\begin{cases} \dot{T} = \lambda \cdot T \cdot (1 - \frac{T}{V}) - T \cdot (PD_{Cis}(C_{Cisplatin}) + PD_{Pem}(C_{Pemextrexed})) \\ \dot{V} = -k \cdot V \cdot (\theta - \frac{T}{V}) \end{cases}$$

| Variable/Parameter | Meaning |
|---|---|
| T | Tumor size |
| V | Vessel density |
| λ | Tumor growth rate |
| k | Angiogenesis rate |
| θ | Equilibrium vascular density |
| $C_{Cisplatin}$ | Cisplatin concentration |
| $C_{Pemextrexed}$ | Pemextrexed concentration |
| $PD_{Cis}$ | Cisplatin PD effects function |
| $PD_{Pem}$ | Pemextrexed PD effects function |

Fig. 5

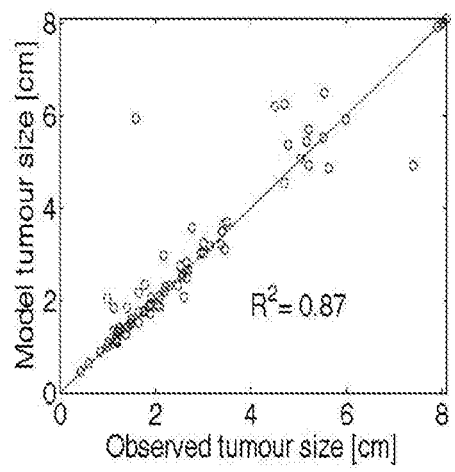
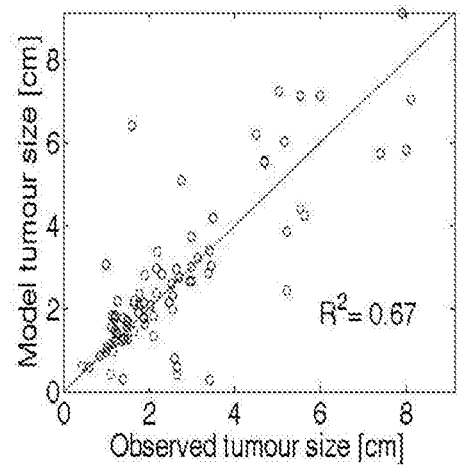
Fig. 6A                    Fig. 6B
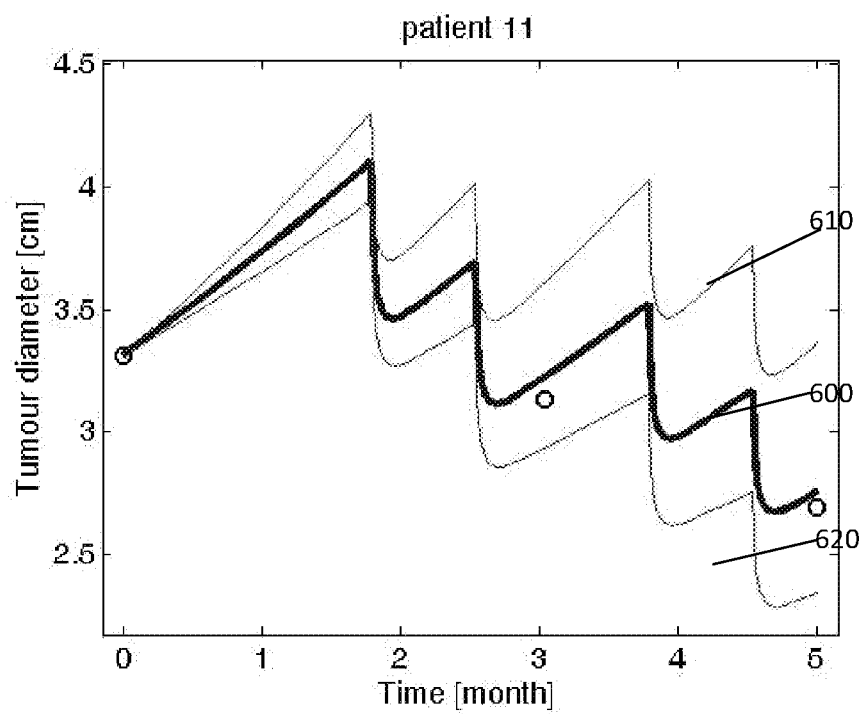
Fig. 7

METHOD AND SYSTEM FOR PREDICTION OF MEDICAL TREATMENT EFFECT

TECHNOLOGICAL FIELD

This present invention relates to a method and system for prediction of treatment effects on progression of disease.

BACKGROUND

Personalized medicine approach has recently become very attractive. Personalized medicine is known as providing "the right patient with the right drug at the right dose at the right time." Personalized medicine thus concerns tailoring of medical treatment to the individual characteristics, needs, and preferences of a patient during all stages of care, including prevention, diagnosis, treatment, and follow-up.

Various techniques have been developed for assisting a physician in selecting a treatment protocol/plan for a specific disease. According to these techniques, when a physician prescribes a specific treatment protocol for treating a disease of a specific patient, he/she may consider, inter alia, a plurality of treatment protocols, statistical data about the effect of the treatment protocols on previously treated patients, medical data of the specific patient including the current disease stage, disease progression data since diagnosis, as well as patient's age, general health, background illnesses, etc. Practically, these techniques are based on statistics from clinical trials and the physician's knowledge and experience for selecting one or more of the known treatment programs for a specific patient with a certain disease.

International patent publication WO 02/32458, describes an earlier technique of the inventor of the present application, aimed at recommending an optimal treatment protocol for an individual. According to this earlier technique, a system model (mathematical model), a plurality of treatment protocols, and a system model modifier are used. The system model is modified based on parameters specific to the individual; and then an optimal treatment protocol is selected from the plurality of treatment protocols based on the modified system model.

GENERAL DESCRIPTION

There is a need in the art for a novel approach in assisting a physician in choosing the most suitable (optimal) treatment protocol/plan for a specific individual and a specific disease.

The need for a novel approach is earnestly solicited in view of the limitation of current technologies in the field for predicting the clinical outcome of a treatment protocol with respect to predetermined one or more endpoints of the treatment plan (at times termed here as treatment targets). The term "endpoint" or "treatment target" used herein actually refers to the treatment goal as defined by a physician, which may be an endpoint of treatment.

The current technologies are mainly based on the statistical and historical data for patients with comparable characteristics to those of the specific individual to be treated, and who suffered from the same illness. Accordingly, these techniques cannot be used as an efficient treatment prediction tool, enabling treatment selection/prediction with respect to a specific patient and disease, and predetermined endpoint(s) other than those evaluated in the past clinical trials.

The present invention solves the above limitations of the known techniques and provides a novel technique for prediction of treatment effect, enabling improvement of patient-specific treatment planning The technique of the invention provides for prediction of response to therapy. To this end, the invention utilizes medical data of a specific individual, data about one or more endpoints, and disease progression model(s), each corresponding to one or more of treatment protocols for treating the specific medical condition. According to the invention, all these data are processed and analyzed to determine a personal treatment effect with respect to one or more of the treatment protocols and one or more of the endpoints. The processing results allow (a physician or an electronic analyzing module) to evaluate the treatment protocols according to each endpoint with respect to the specific individual and specific medical condition, and may for example allow selecting the most suitable treatment protocol. Considering the electronic analyzing module, it may be configured to perform a ranking procedure with respect to the predicted personal treatment effects of multiple treatment protocol. The evaluation (e.g. electronic ranking) indicates a degree of success of a certain simulated treatment protocol in the achievement/approaching of the predefined one or more endpoints. The endpoints considered in the present invention may include, e.g. survival, stop of tumor growth, tumor size over time, time to disease progression, time or time profile of the individual's reaction to certain drug, etc. The treatment protocol may for example include treatment by a single drug or combination of drugs, such as chemotherapy, biological therapy, immunotherapy and others.

The terms "medical data", or at times termed "medical metrics" used herein refer to certain parameters/conditions of a specific individual. Such medical data include one or more of the following: medical history, physical examination (e.g. age, weight, height, gender, etc.). In some embodiments, the medical data of the specific individual also include the pretreatment clinical data of the specific individual, which may also include the disease-related clinical data, e.g. pathology review, histologic subtype; imaging data; blood counts (CBC); biochemistry profile; hormone profile and markers of inflammation; tumor markers; molecular diagnostic tests; Immunohistochemical Staining (IHC); gene status, such as mutation in one or more genes, one or more amplification in one or more copies, genetic recombination, partial or complete genetic sequencing; and death indicator. One or more anticipated treatment regimens may also be included, e.g. chemotherapy drugs, immunotherapy drugs, biological drugs, combination of two or more drugs.

According to the present invention, a personalized disease progression model is achieved by utilizing a set of equations (e.g. differential equations) that describe the disease progression in time and disease interaction with particular treatment protocol(s). Prior to adaptation to the individual patient, the set of equations forms a population model representing a uniform general mechanistic model applicable for all patients. The general population model is modified to allow adaptation to each individual patient based on the patient's personal medical data. The modification of the general population model may be achieved by employing algorithms of machine learning which are trained using training data sets that include large number of patients who were treated by the treatment protocols under examination.

Thus, according to a broad aspect of the present invention, a computerized system is provided for use in planning a medical treatment for an individual under specific medical condition (disease), the system comprising:

a data input utility configured for receiving input data comprising: first input data comprising medical data of a specific individual, and second input data comprising data indicative of at least one endpoint of treatment;

a data processor configured for utilizing said medical data of the specific individual and said data indicative of the at least one endpoint and processing disease progression models, each corresponding to a treatment plan comprising one or more predetermined treatment protocols for treating said specific medical condition, and generating data indicative of personal treatment effect with respect to each of said treatment plans and said at least one endpoint; thereby enabling evaluation of said treatment plans.

The disease progression models that are processes are actually modified disease progression models which are based on training data set(s) of medical data of a group of treated patients (clinical data). Such modified disease progression models may be previously prepared (as will be described below) and stored in a database, and accessed to apply thereto an individualization processing, i.e. applying the medical data of the specific individual and the data indicative of the at least one endpoint. The data processor thus may or may not include a modifier module capable of providing said modified disease progression models. In case the data processor includes such modifier, it may be capable of using certain initially provided data about basic disease progression models (e.g. reference or standard disease progression models) and utilizing training data set(s) of medical data of a group of treated patients (clinical data) to create the modified disease progression models. As for the initially provided disease progression models, they may be taken from a storage device as reference data, or may be created by the data processor in a conventional manner using population models. The modified disease progression models are determined by using the medical data of the group of treated patients and applying machine learning together with the basic (initial) disease progression models.

The process of modifying the basic disease progression models, by training the models using the training data set(s) of medical data of a group of treated individuals, provides functions describing relations between the medical data of the group of individuals and variations of one or more components (parameters) in the modified disease progression models, each relating to a specific treatment plan of the specific medical condition. These functions form integral part of or define the modified disease progression model(s), enabling the personalization of the modified disease progression models for a specific individual/patient, as will be further described below.

The data processor includes a predictor module configured and operable for individualizing each of the modified disease progression models, that by utilizing the medical data of the specific patient, and thus creating a personalized disease progression model. These personalized disease progression models can then be simulated using appropriate simulator/analyzer module with respect to the treatment target(s) (treatment goals or endpoints) to thereby evaluate the effects of the one or more treatment plans/protocols included in each personalized disease progression model for the specific patient and specific disease in accordance with the predefined endpoint(s).

As indicated above, the system may further comprise an analyzer module configured for analyzing the output data and ranking the treatment plans according to each endpoint with respect to the specific individual and the specific medical condition, and generating ranking data.

The data indicative of the disease progression models comprises modified data of reference disease progression models based on medical data of a group of individuals and functions describing relation between the medical data of the individuals and variations of one or more components in the one or more standard disease progression models. The data indicative of the disease progression models thus comprise modified disease progression models.

In some embodiments, the system is adapted for obtaining the modified disease progression models from a database. In some other embodiments, the data processor comprises a modifier utility which is configured for modifying the standard disease progression models based on training utilizing the medical data of the group of individuals and creating functions describing relations between the medical data of the individuals in the group and variations of the one or more components in the one or more reference disease progression models, and generating the modified disease progression models.

The data processor comprises a predictor module configured and operable for individualizing the data indicative of the disease progression models by utilizing the medical data of the specific patient, and creating a personalized disease progression model. Such personalized disease progression model may be further simulated with respect to one or more endpoints to thereby evaluate the personalized disease progression for each treatment for the specific patient and the specific disease.

The system may further comprise a communication utility for communicating with a database for accessing reference data comprising the treatment protocol(s) as well as the data indicative of one or more disease progression models. Each disease progression model is based on a population model with respect to the specific medical condition. The population model comprises data indicative of disease progression for untreated population, pharmacokinetics and pharmacodynamics of drugs used in treatment plan(s), and response to treatment for treated population.

The medical data of the specific individual may comprise data indicative of at least one of the following: past medical data; physical examination; pathology review; histologic subtype; imaging data; blood counts (cbc); biochemistry profile; hormone profile and markers of inflammation; tumor markers; molecular diagnostic tests; immunohistochemical staining (ihc); gene status, mutation in one or more genes, one or more amplification in one or more copies, genetic recombination, partial or complete genetic sequencing.

The medical data may further comprise at least one of the following: an inter-dosing interval, drug dose, PK and PD information of one or more treatment regimens, each comprising at least one of chemotherapy drug, immunotherapy drug, or biological drug.

The medical data of the group of individuals typically comprises data indicative of at least one of the following for each individual: past medical data; physical examination; pathology review; histologic subtype; imaging data; blood counts (cbc); biochemistry profile; hormone profile and markers of inflammation; tumor markers; molecular diagnostic tests; immunohistochemical staining (ihc); gene status, mutation in one or more genes, one or more amplification in one or more copies, genetic recombination, partial or complete genetic sequencing; death indicator.

The medical data of the group of individuals may further comprise at least one of the following: inter-dosing interval, drug dose, PK and PD information of one or more treatment regimens, each comprising at least one chemotherapy drug, immunotherapy drug, or biological drug.

The imaging data preferably comprises images at different times of a body part or organ.

The endpoint(s) may comprise at least one of the following: survival, growth arrest of tumor, changes in tumor size over time, time to disease progression, time or time profile of the individual's reaction to one or more selected drugs.

According to another broad aspect of the invention, there is provided a computerized system for use in planning a medical treatment for an individual under specific medical condition, the system comprising:

a data input utility configured for receiving input data comprising medical data of a group of individuals treated with respect to said specific medical condition, and comprising data about one or more reference disease progression models;

a data processor comprising a modifier module configured and operable for processing the input data, determining functions describing relations between the medical data of the group of individuals and variations of one or more components in one or more reference disease progression models, and utilizing the functions to generate modified disease progression models, enabling personalization of the modified disease progression models.

The invention, in its yet further aspect provides a method for use in planning a medical treatment for an individual under specific medical condition, the method comprising:

providing first input data comprising medical data of a specific individual, second input data comprising data indicative of at least one endpoint;

providing reference data indicative of one or more predetermined treatment protocols with respect to said specific medical condition;

providing data indicative of disease progression models with respect to said specific medical condition;

utilizing said medical data of the specific individual and said data indicative of the at least one endpoint and processing said data indicative of disease progression models, each corresponding to a treatment plan comprising said one or more predetermined treatment protocols for treating said specific medical condition, and generating output data indicative of personal treatment effect with respect to each of said treatment plans and said at least one endpoint, thereby enabling selection of the treatment protocol for the specific patient and specific disease.

More specifically, the present invention can be used for evaluating cancer disease drug treatments, e.g. lung cancer, and is therefore exemplified below with respect to this specific application. It should, however, be understood and as also clear from the description below, that the invention is not limited to any specific disease as well as any specific patients' group, provided there exists at least one treatment protocol for a disease that is to be treated and there exists patient-specific medical data.

BRIEF DESCRIPTION OF THE DRAWINGS

In order to better understand the subject matter that is disclosed herein and to exemplify how it may be carried out in practice, embodiments will now be described, by way of non-limiting example only, with reference to the accompanying drawings, in which:

FIG. 5 is an example of defining a disease progression model used in the present invention, FIGS. 6A-6B and 7 illustrate the experimental results of using the technique of the invention for predicting the tumor size dynamics, FIGS. 6A and 6B showing fitted and observed tumor sizes based on the modified disease progression models and FIG. 7 showing tumor size dynamics prediction by a personalized disease progression model created using an embodiment of the present invention.

DETAILED DESCRIPTION OF EMBODIMENTS

Figure 1:
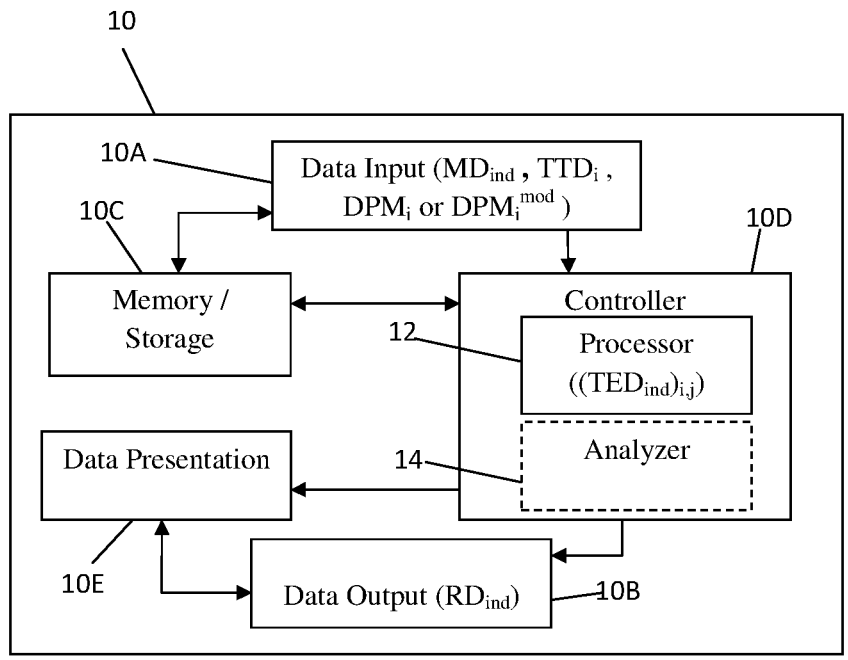
FIG. 1 is a block diagram of a system according to the present invention for planning a medical treatment for a specific patient.

The invention provides a novel technique for use in planning a medical treatment for a specific individual/patient under specific medical condition (disease). Reference is made to FIG. 1 illustrating schematically, by way of a block diagram, one example of a planning system 10 of the present invention. The system 10 is a computerized system, including inter alia such utilities (software and/or hardware) as data input and output utilities 10A, 10B, memory utility 10C, controller 10D, and data presentation utility (e.g. display) 10E.

The system 10 receives certain input data, being provided by user (e.g. physician) and/or from an external device (not shown). Accordingly, the input utility 10A is appropriately configured to include user interface as well as a communication port/interface (which are not specifically shown) for communication with external devices (e.g. storage device/database, medical measurement device, server, etc.) via wires or wireless network signal transmission (e.g. RF, IR, acoustic, etc.). All these components and their operation are known per se and therefore need not be specifically described, except to note the following: For the purposes of the invention, the input data utilized for personal treatment prediction include first input data comprising medical data $MD_{ind}$ of a specific individual, second input data comprising data indicative of one or more endpoints, generally at $TTD_i$ (i being the number of an endpoint in the list of I endpoints, i.e. I≥1), and data about one or more modified disease progression models, generally $DPM_j^{mod}$ (j being the number of a disease progression model in the list of J disease progression models, i.e. J≥1). As will be described below, $DPM_j^{mod}$ is actually a modification of a so-called "basic data" of the reference or standard disease progression model $DPM_j$.

The medical data $MD_{ind}$ of a specific individual are typically received via user input (e.g. physician) or from a storage device where such data has been prepared/collected, or directly from one or more measurement/monitoring devices. As will be described more specifically further below, the medical data of the specific individual include physical parameters/conditions of the individual and may also include disease-related clinical data of the individual (as specified above). The endpoint data $TTD_i$ can also be based on physician input (e.g., selection from a previously stored list of endpoints).

Generation of the disease progression models $DPM_j^{mod}$ by modification of the basic models $DPM_j$ is exemplified further below. Generally, such disease progression models $DPM_j$ or $DPM_j^{mod}$ may be obtained via communication with storage device/ utility (internal or external) or determined by the system 10. Each of the disease progression models corresponds to treatment of the specific medical condition (disease) based on one or more treatment protocols $TP_k$ (k being the number of a treatment protocol in the list of K treatment protocols, i.e. k=1, . . . K). Therefore, the disease progression models may include data about one treatment protocol $TP_k$, or data about a combination of more than one treatment protocol $TP_k$. The treatment protocols $TP_k$ typically correspond to known (standardized) treatment protocols used in the field of the specific medical condition. Generally, the treatment protocols or at least some of them may be specifically tailored by the treating physician, in accordance with the common practice in the field. In the simplest case, the number of the disease progression models $DPM_j$ (as well as $DPM_j^{mod}$) is equal to the number of the treatment protocols $TP_k$ (J=K), in case each disease progression model includes data corresponding to one treatment protocol. Generally, however, the numbers may be different, e.g. some or all of the disease progression models include data corresponding to a plurality of treatment protocols.

According to the invention, the controller 10D comprises a processor 12 configured for processing each of the modified disease progression models $DPM_j^{mod}$ (or may also perform pre-processing of the basic models $DPM_j$ for obtaining the properly modified models $DPM_j^{mod}$) utilizing the medical data $MD_{ind}$ of the specific individual and the endpoint data $TTD_i$, resulting in personal treatment effect data $TED_{ind}$ for each of at least some of the treatment protocols $TP_k$ and one or more of the endpoints $TTD_i$. Thus, the processing results may include $(TED_{ind})_{i,j}$ different personal treatment effects. For example, considering that all the modified disease progression models $DPM_j^{mod}$ have been processed (e.g., simulated) for all the endpoints $TTD_i$, then the total number of the personal treatment effects gained would be I×J. The processor 12 generates output data indicative of the predicted personal treatment effects for each endpoint per each treatment plan/protocol. This output data is configured/formatted to enable analysis of this data and ranking the treatment plans according to each endpoint with respect to the specific individual and the specific medical condition.

The controller 10D may thus further include an analyzer module 14 configured for analyzing the data $(TED_{ind})_{i,j}$ indicative of the personal treatment effects with respect to the endpoint(s) for treatment protocols and ranking the treatment protocols $TP_k$ according to each endpoint with respect to the specific individual and specific medical condition, producing output ranking data $RD_{ind}$, enabling the physician to select the preferred treatment protocol(s) in accordance with the endpoint or a relation between two or more predefined endpoints. It should be understood that in case the physician has defined more than one endpoint, they may also be assigned respective weighting factors defining a relation between them.

Figure 2:
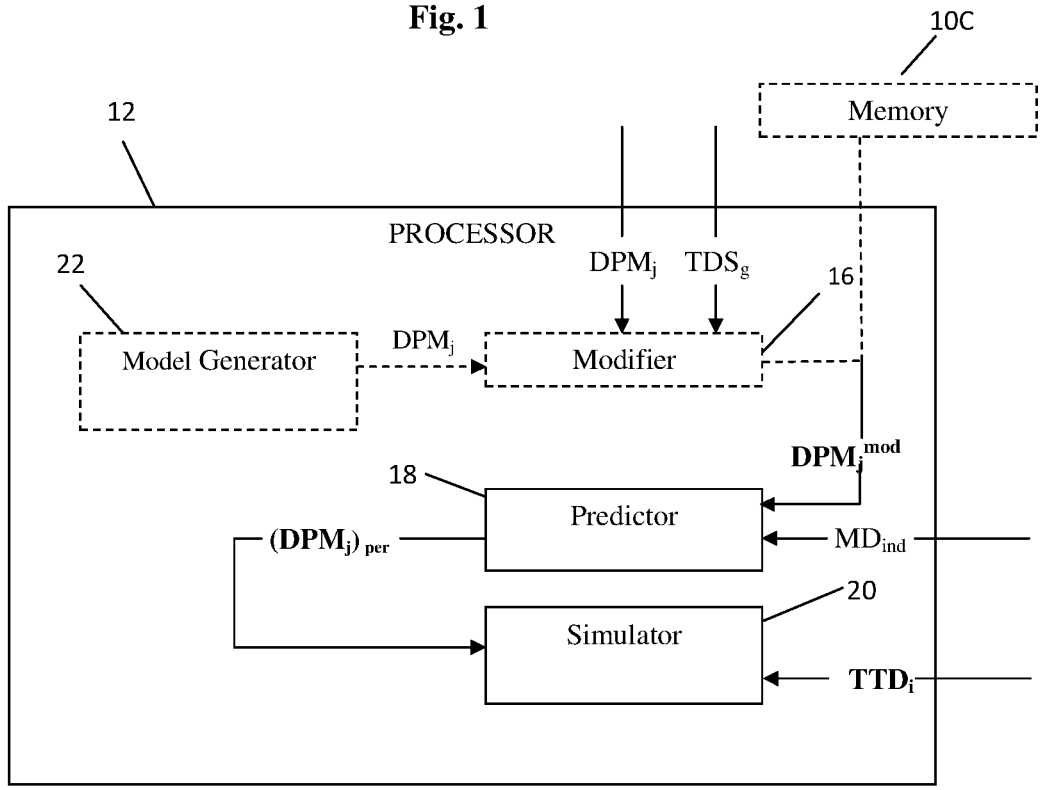
FIG. 2 is a block diagram of a data processor suitable for use in the system of the present invention.

Referring to FIG. 2, there is shown an example of the configuration and operation of the processor 12. The processor includes a predictor module 18, and in this example also optionally includes a modifier module 16, as well as a simulator module 20. The modifier module 16 is configured as an expert system, and operates to receive the data about basic (standard) disease progression models $DPM_j$ as an input, applies machine learning thereto and produces, and produces for each disease progression model $DPM_j$, a modified disease progression model $DPM_j^{mod}$. To this end, the modifier module 16 utilizes a further input data (e.g. received from the database) including training data sets $TDS_g$. Each such training data set $TDS_g$ includes medical data of a group of patients (e.g. 100 patients) treated by one or more of the treatment protocols $TP_k$. As such, the training data set $TDS_g$ may include for each member of the group of patients, as has been mentioned above, one or more of the following: medical history, physical examination (e.g. age, weight, height, gender, etc), pretreatment clinical data which may also include the disease-related clinical data, e.g. pathology review, histologic subtype, imaging data, blood counts (CBC), biochemistry profile, hormone profile and markers of inflammation, tumor markers, molecular diagnostic tests, immunohistochemical staining (IHC), gene status, treatment regimen and death indicator.

The modifier 16 provides modified disease progression model(s) $DPM_j^{mod}$. The modified disease progression model is created by selecting the training data set for the treatment protocol(s) matching a corresponding one of the disease progression models, and updating at least some of the components (parameters) of the disease progression model using the respective training data set, resulting in the modified disease progression model $DPM_j^{mod}$. Such modified disease progression model $DPM_j^{mod}$ actually includes a function F (based on the large training set data $TDS_g$, i.e. medical/clinical data of the group of individuals) describing a relation between medical data of the individuals in the group and variation of components $C_j$ (e.g., model parameters) in the disease progression models $DPM_j$.

Generally, the modification of disease progression models based on the training data set and creation of modified disease progression models may be previously done for each treatment protocol and each basic disease progression model, and such modified disease progression models are thus saved in the external database or in the memory of the system. In other words, the modification of disease progression models is carried out prior to be applied to the individualized prediction process for the specific patient. Thus, generally, the modifier module 16 provides the modified disease progression models (either taking them from the memory, or specifically preparing, as the case may be). The preparation of such modified models uses machine-learning and determination of functions describing relation between the large training set data (medical/clinical data of the group of individuals) and variation of components in the disease progression models.

The predictor module 18 is configured for processing the modified disease progression models $DPM_j^{mod}$ using the input medical data of the specific individual $MD_{ind}$ (e.g. received from memory of system or external storage device or directly from a measurement device, as the case may be), and generating, for each modified disease progression model $DPM_j^{mod}$, a personalized disease progression model $(DPM_j)_{per}$. Such personalized disease progression model is actually obtained by replacing the medical data of the group of individuals, $TDS_g$, by the medical data of the specific patient $MD_{ind}$.

Further provided in the processor 12 is the simulator 20, which is adapted for simulating each of the personalized disease progression models $(DPM_j)_{per}$ with respect to the endpoint(s) $TTD_i$. The simulation results are then analyzed in the analyzer module 14.

As shown in FIG. 2 in dashed lines, the processor 12 may also include a model generator module 22, which is capable of generating disease progression models $DPM_j$ and/or $DPM_j^{mod}$. (The creation of the basic disease progression models $DPM_j$ may be done in the conventional manner, as described in the example below. As indicated above, the provision of such model generator module 22 is optional as the standard disease progression models ($DPM_j$) may be obtained as input data from the storage utility 10C or another external storage. As also indicated above, the modified disease progression models $DPM_j^{mod}$ may also be created once, using the above-described technique of the invention, and stored in the memory.

Figure 3:
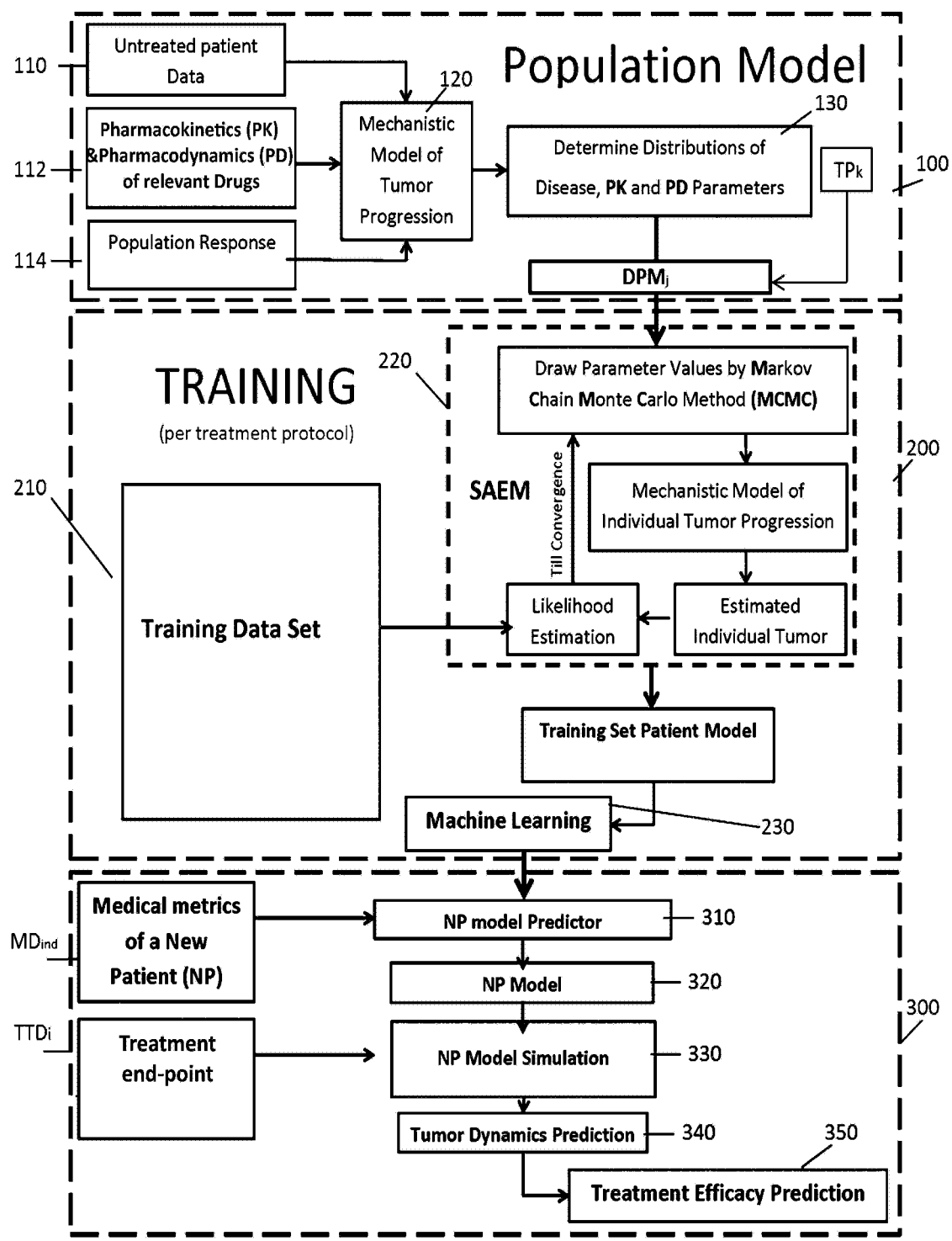
FIG. 3 is a flow diagram of an example of a method of the invention for planning a medical treatment for a specific patient, FIG. 4 exemplifies a simplified graphical scheme of an exemplary mathematical model describing tumor progression under treatment in locally advanced/advanced NSCLC patients.

Reference is now made to FIG. 3 exemplifying a flow diagram of a method of the invention for selecting the most suitable treatment for a specific patient. Generally, the method of the invention provides for selecting the most suitable treatment for a specific patient and specific disease, utilizing a novel technique for prediction of treatment effect. As indicated above, the prediction technique utilizes, as one of the input data pieces, disease progression models $DPM_j$ presenting reference data obtainable from a storage device/database. As also indicated above, the system of the invention may be capable of generating the disease progression models $DPM_j$ instead of or in addition to those obtainable in the database. In the present example of FIG. 3, a possible way of building the disease progression models $DPM_j$ is exemplified. As further shown in FIG. 3, the method of the invention includes creation of modified disease progression models $DPM_j^{mod}$ based on the training data sets, and further creation of the personalized disease progression models $(DPM_j)_{per}$ based on the modified disease progression models $DPM_j^{mod}$ and the medical data of the specific patient, in order to obtain the treatment effect data $TED_{ind}$ for the individual under each of the examined disease progression models and obtain the ranking data $RD_{ind}$ thereof.

For simplicity only, not limiting the scope of the invention, in the following lines each disease progression model $DPM_j$ as well as $DPM_j^{mod}$ will be considered as including data about one treatment protocol $TP_k$, and they may be interchangeably used. Also, the process (algorithm) shown in FIG. 3 exemplifies treatment of cancer, however this should not be considered as limiting the invention in any way.

According to the specific but not limiting example of FIG. 3, three major stages are performed in order to obtain the ranking data $RD_{ind}$ of the treatment protocols $TP_k$. These include: the first stage 100 of providing the reference disease progression models $DPM_j$, the second stage 200 of providing the modified disease progression models $DPM_j^{mod}$, and the third stage 300 of creation of the personalized disease progression models $(DPM_j)_{per}$ according to the invention, enabling further simulation of these personalized disease progression models $(DPM_j)_{per}$ in conjunction with the endpoint data, and ranking the results. It should be understood that the stage 100 is an optional one, and the stage 200 may be carried out once, using the reference disease progression models $DPM_j$ stored in the memory, creating the modified disease progression models $DPM_j^{mod}$ and storing them to be accessed each time for stage 300.

The provision of each of the reference/basic disease progression models $DPM_j$ (stage 100) may include adjusting a population model for a specific treatment protocol. The second stage 200 includes creation of the modified disease progression models $DPM_j^{mod}$ according to the invention, as described above. More specifically, the population model 100 may be created once for a specific medical condition, and is obtained by utilizing data of a large number of patients under said specific medical condition. The population model 100 includes untreated disease progression data 110 which is the data about disease progression in untreated patients 110, Pharmacokinetics (PK) and Pharmacodynamics (PD) of relevant drugs 112 which is the data about drugs typically used in the treatment of the specific medical condition, and population response to treatment 114 which is statistical data regarding treated patients treated by known treatment protocols. The data utilized for creation of the population model may include all the available data from clinical practice and clinical trials, as well as medical research relating to the specific medical condition. From these three data portions 110, 112 and 114 a general mechanistic model of the disease progression (e.g. tumor size evolution in time) 120 is obtained and used in order to determine population distributions of disease, and PK and PD parameters 130.

These distributions 130 are then applied to each of the set of pre-defined (known) treatment protocols $TP_k$ to obtain the disease progression model $DPM_j$ for each treatment protocol $TP_k$. Each disease progression model $DPM_j$ describes, inter alia, the progress in time for the specific medical condition when treated by a specific treatment protocol $TP_k$ (or plurality of protocols).

In the second, training stage 200, which as mentioned above can be carried out once or in several stages of updating, each disease progression model $DPM_j$ is modified (updated), through application of an iteration process 220 utilizing the training data set(s) $TDS_g$ 210. As mentioned above, each training data set involves data of large number (typically hundreds) of patients who were treated by the treatment protocol(s) included in the specific disease progression model. The iteration process 220 includes the following steps in the order shown, till convergence: drawing model parameters values (e.g. by Markov Chain Monte Carlo Method (MCMC)), generating mechanistic model of individual disease-parameter progression (e.g. tumor size evolution in time), estimated disease progression (e.g. individual tumor size) and likelihood estimation. According to the invention, modifying one or more components (parameters/coefficients) of the disease progression model $DPM_j$ includes creating one or more functions, each such function describing relations between the corresponding training data set and components' variations (parameter's ranges) in the disease progression model. As indicated above, the modification procedure also utilizes machine learning functions 230 of the data processor, to thereby determine such functions and generate the modified disease progression models $DPM_j^{mod}$ to be used in the personalized prediction stage 300.

In the third stage 300, each modified disease progression model $DPM_j^{mod}$ is processed (step 310) utilizing the personal medical data $MD_{ind}$ (medical metrics), and the personalized disease progression model $(DPM_j)_{per}$ is generated (step 320). The personalized disease progression model $(DPM_j)_{per}$ is a model version ready for simulation in conjunction with each of the selected endpoint(s) $TTD_i$ (step 330), to obtain the treatment effect (e.g. specific tumor dynamics prediction) 340, specific to the individual, the treatment protocol and the endpoint.

The treatment effect results of all the simulated personalized disease progression models $(DPM_j)_{per}$ for each selected endpoint $TTD_i$ then undergo ranking to obtain treatment efficacy prediction 350 for the specific individual. The treatment efficacy prediction 350 may be in the form of a ranking table that lists the treatment protocols against the endpoint, where different endpoints may be assigned with corresponding weighting factors. In other words, it might show that for a first endpoint, a first treatment protocol (or a combination thereof) has the highest performance, while for a second endpoint a second treatment protocol (or a combination thereof) has the highest performance, for the same individual.

The following is a specific but not limiting example of the technique of the present invention. As indicated above, the invention may be used for predicting/selecting most suitable treatment of cancer, e.g. lung cancer, for a specific patient (the term specific patient is at times referred to as a certain individual).

Lung cancer (LC) is the most commonly diagnosed cancer: approximately 1.6 million new cases being diagnosed each year worldwide. During 2013, an estimated 228,190 new cases of LC were expected to be diagnosed in the United States alone, representing almost 14 percent of all cancer diagnoses in the country. LC has the highest mortality rate among all cancers, in the United States, causing nearly one-third of all cancer-related deaths. Given the incurable nature of LC, it is considered a terminal illness with a five-year survival rate of about 16%.

LC is divided into two major classes; small-cell lung cancer (SCLC) and non-small-cell lung cancer (NSCLC) that accounts for more than 85% of all LC cases. NSCLC is further classified into four main types: squamous cell carcinoma, adenocarcinoma (ADC), bronchioalveolar and large cell non-differentiated carcinoma. ADC is the most common form of LC in the United States among both men and women. Only 15% of the LC patients are diagnosed at localized stage, 22% are diagnosed after spread to regional lymph nodes (LN) and the majority, about 57%, are diagnosed at an advanced stage, stages III/IV, when the cancer has already metastasized (for the remaining 8% the staging information was unknown).

The standard therapy for patients with early stage NSCLC of ADC histology, is radical resection with or without the addition of adjuvant platinum-based chemotherapy. However, most patients with NSCLC are diagnosed when the cancer is already locally advanced/advanced (stage IIIB/IV), so that surgical resection is not an option, and chemotherapy is used. The 1st line treatments for inoperable ADC patients are platinum agents (cisplatin or carboplatin) in combinations with one of the following drugs: taxanes (paclitaxel, docetaxel), vinorelbine, pemetrexed, or gemcitabin. In the United States, the 1st line treatment is most often cisplatin+pemetrexed (to be denoted C+P), carboplatin+pemetrexed, or carboplatin+paclitaxel. In an effort to extend survival, when initial response is observed, the 1st line treatment is followed by a maintenance therapy containing pemetrexed or the biological drugs, bevacizumab or cetuximab. In the case of progressive disease, the patient is directed to 2nd, 3rd . . . line chemotherapies that have less clear guidelines and can be any of the listed drugs that were not used previously for this patient; additionally, radiotherapy may be offered. In addition to the chemotherapy drugs, specific target therapies have been developed for the treatment of advanced ADC. These therapies include drugs that target the epidermal growth factor receptor (EGFR; e.g., erlotinib, gefitinib), drugs that targets anaplastic lymphoma receptor tyrosine kinase (ALK; e.g., crizotinib), or a drug that targets the vascular endothelial growth factor (VEGF; e.g., cetuximab, bevacizumab). Yet, despite the many new chemotherapy and targeted drug options available, little progress has been made in improving the survival of NSCLC patients over the last decades, and long-term prognosis of patients with distant NSCLC remains poor, with five-year survival rate being less than 10%.

Until recently the National Comprehensive Cancer Network (NCCN) guidelines for the management of NSCLC had been rather obscure, but today a global attempt is made, to tailor the management of the cancer according to the specific patient's characteristics. Indeed, recent advances in understanding both tumor biology of NSCLC and mechanisms of action (MOA) of various drugs, have led to initiation of personalized treatment in patients with NSCLC. However, even though many potential selection factors for customizing systemic treatment in advanced NSCLC were tested, only histology type, EGFR mutation or ALK rearrangement status have been validated as predictive markers. Most patients do not present EGFR or ALK mutations, and physicians choose the treatment according to tumor histology, stage and patient-specific clinical factors, such as age, pulmonary function, and comorbidity. The NCCN guidelines give recommendations for any part of the treatment. Yet, multiple treatment options are available at any clinical decision-making junction, and the choice among them is still based on experience and intuition of the physician. This makes oncology "more an art than science".

Early insight into the patient's anticipated response to various treatment options can be crucial for properly planning a cost-efficient therapeutic strategy, distinguishing between those patients most likely to benefit from a given treatment and those who may incur cost and suffer side-effects without being helped by the therapy. Such forecast may offer hope for diminished duration and severity of illness and improved success rates, and at the same time, it may reduce healthcare costs by improving the ability to quickly and reliably select effective therapy for a given patient while minimizing the cost associated with ineffective treatment and avoidable adverse events.

Considering the heterogeneity of human cancer, it is well accepted that the 'one-size-fits-all' approach is suboptimal, emphasizing the need for personalized cancer therapy. But, in spite of its great promise, personalized oncology still faces many hurdles, and it is increasingly clear that molecular biomarkers alone do not constitute a sufficient tool for achieving significant clinical improvement. The ability of such biomarkers to provide accurate prognosis of an individual cancer patient, and to anticipate his/her response to any treatment, is still poor. One reason for this is that the clinical biomarkers do not affect the patient response directly, but rather, via their effects on the complex disease dynamics, so that the true weight of the biomarker in the overall patient's response is obscured. Computational methods can "open the black box" by crystallizing, on the one hand, the relations between biomarkers and disease dynamics parameters, and on the other hand, the relations between disease dynamics parameters and the patient response.

The few available statistical tools for prognosis in NSCLC patients (e.g. Personalized Rx online, Myriad myPlan), or mixed-effects models, are based merely on standard statistical analysis of past clinical trials. These tools, rather than modelling dynamical processes, analyze retrospective patients' data where specific end-points (i.e. survival) were monitored. Thus, they are limited to prediction of a patient's state at only a few predetermined time-points, for exactly the same treatment types and regimens that were historically applied. According to the invention, in contrast, more accurate and informative individual prognosis and more versatile response predictions for NSCLC patients are provided, including for potentially altered treatment regimen. Statistical analysis of large patient databases is merged with complex (dynamic/mechanistic) ordinary differential equation (ODE) modeling. This endows: (1) larger predictive capability, as the algorithm developed on the basis of this technology encompasses more complex processes underlying NSCLC and MOA of the drug; (2) more reliable predictions for the individual patients, using higher correlations between patient data (including biomarkers, such as EGFR, ALK, KRAS) and the individual patient's response (e.g., by predicting synergistic effects of a few biomarkers, even of different types, each one being insignificant on its own); (3) less direct reliance on data (and smaller susceptibility to errors or bias in data), as the mathematical model itself is based on in-depth understanding of the underlying biology. As such, the invention provides a predictive algorithm to forecast the effects of any available or anticipated drug treatment protocol.

The invention advances beyond the current mathematical and statistical modelling frontier. The algorithm contains a retrospectively validated mathematical mechanistic model for NSCLC and its treatment, which has both a population model component and a patient-specific one (personalized disease progression model). Current mathematical models for lung cancer have been mostly oriented toward drug development. For this reason, these models, characteristically, take the form of relatively complex pharmacodynamic (PD) models, and simplistically described tumor progression models, typically by single-equation growth law. These models can be used to describe general response to drug in patient populations, but they fall short of adequately describing drug-patient interactions and personalized disease progression dynamics in particular patients. For this reason they cannot be employed for predicting changes in the pathology of single patients Similarly, standard mixed-effects modeling has mostly been applied in evaluating pharmacokinetics (PK) of a drug, with only a few models describing drug PD; those applications are also oriented towards drug development and regimen design. The prevailing mixed-effects modelling methodology uses simple mathematical description of cancer growth, and focuses on a good population description. However, given the large inter-patient variability, this focus blurs the inability of such models to provide a precise mathematical description of the process on the individual level.

In contrast, in the invention the mathematical modelling strategy is oriented toward the clinic. Essentially, this strategy concerns the creation of specific patients' models (modified disease progression models) and their simulations for predicting various aspects of the individual response to treatment (personalized disease progression model). This is done, in essence, by: (i) creating a mechanistic mathematical model for drug-patient interactions (disease progression models), (ii) using large patients databases to identify functions that relate clinical metrics to disease progression models, (iii) applying these functions to relate the single patient's metrics to his/her personalized disease progression model and (iv) simulating the personalized disease progression model to generate specific response predictions (endpoints) for the patient. The invention's mixed-effects modeling methodology accurately describes the complexity of disease progression in individual patients by introducing mechanism-based mathematical models into mixed-effects framework. To this effect, the inventors use advanced methods (e.g., alternative modeling, machine learning) and criteria from information theory to identify the most reliable model that can predict personal response to the treatment, and be implemented in the clinic. This is the first attempt to develop a technology that uses mixed-effects modeling for a real-time clinical purpose in individualized medicine, rather than for drug development.

Although targeted treatments offer improved efficacy and tolerability for LC patients with an identified mutation, for the majority of patients no targetable mutations are established. The benefits of standard chemotherapy for advanced LC are limited, in terms of both life expectancy and quality of life. Moreover, the cost of such treatments is an especially important consideration in an era of increased emphasis on achieving an acceptable balance between the costs and benefits of medical interventions. The economic burden of patients with metastatic lung cancer receiving chemotherapy is substantial, exceeding $125,000 per patient. Chemotherapy and other outpatient medication account for 22% and 24% of total costs, respectively. Using the invention to target chemotherapy treatments only to those patients that are expected to respond, and finding the most beneficial chemotherapy for each patient, will help direct these costly treatments more effectively. In addition, reduction of the number of treatment cycles to what is necessary for survival is expected to increase the cost-effectiveness of chemotherapy for NSCLC.

The inventors have thus applied the above-described novel personalized prediction process, for prediction of response to therapy in advanced NSCLC. This algorithm opens the black box mediating between the patient's medical data (e.g., biomarkers) and his/her response. By integrating information taken from large clinical datasets (training data sets $TDS_g$) and disease progression models based on diverse patient populations with literature information on the biological processes and mechanisms in NSCLC (population model) as well as treatment protocols, mathematical formulae are created, which reflect the effects of the individual patient's characteristics and markers on his/her disease progression and, consequently, on the individual response. This approach unravels direct relationships between medical data of the specific patient (such as biomarkers) and specific biological processes governing the response to treatment protocol(s). Personally adjusted models enable a prompt and non-intuitive in silico personal predictions of efficacy under various treatment options. Predicting who will favorably respond to a specific medical therapy, based on patient' specific genetic, anatomical and physiological characteristics, paves the way for personalized medical treatments. This can allow custom-built treatment designed for individual patient anatomic and physiological characteristics.

The inventors have developed and applied their personalization algorithm for predicting response to therapy of locally advanced/advanced NSCLC patients, based on their pre-treatment clinical data (medical data/metrics about specific individual). This technique may be used for a specific patient, as well as a small group of patients. The algorithm developed by the inventors can assist doctors in clinical decision-making, by providing reliable predictions of the individual patient's response to different available and new therapies. The algorithm is based on the above-described nonlinear mixed-effects statistical/mathematical modelling methodology (NLMEM), analyzing patient response on the population scale, for deriving the model of the individual patient, thus predicting the individual response.

The inventors have developed an algorithm that predicts the individual response of locally advanced and advanced NSCLC patients of ADC histology to a 1st line treatment (C+P combination), based on their pretreatment clinical data (medical metrics of the individual). The algorithm development included construction of a mechanistic mathematical model of disease progression under the combination protocol and its integration with a statistical model that correlates between the personal clinical markers and parameters of the individual model within the NLMEM framework. The predictive algorithm was trained by clinical data sets from various sources, and was validated by retrospective data of NSCLC patients. This work is described hereafter.

The basic mathematical model of NSCLC progression under treatment (disease progression model based on population model) is a model where the growth rate of the tumor is affected by the internal vascular system, which, in turn, is regulated by angiogenic factors, including VEGF and platelet-derived growth factor (PDGF), which, both secreted by tumor cells, are, respectively, involved in the generation and in the maturation of blood vessels. The modified disease progression model generated and used in the invention reflects these relationships between the tumor and the vascular system, as well as the mechanism of action (MOA) of the drug; in this modified disease progression model cisplatin and pemetrexed have each drug-specific PK/PD, and both directly reduce tumor size, in a concentration-dependent manner A graphical representation of the mathematical model (modified disease progression), and its main assumptions, is depicted in FIG. 4 showing a simplified scheme of the mathematical model for tumor progression under treatment in locally advanced/advanced NSCLC patients (training set). As shown in the figure in a self-explanatory manner, the modified disease progression model describes a model of disease progression through interactions between the tumor mass 300 and its vascular support 310, and a treatment PK/PD model 320 entailing response to drug therapy, in this case, C+P. The assumptions taken into account in the modified disease progression model are as follows. The tumor growth is regulated by internal vasculature; at equilibrium, both the tumor and the vessel density grow at a certain rate. The tumor overgrowth leads to hypoxia, which triggers secretion of angiogenic factors (such as VEGF) and encourages the angiogenesis process. The vessel overgrowth results in accelerated tumor growth, due to improved nutrient supply. Cisplatin or Pemetrexed assert their unique effect by the reduction of tumor mass.

These assumptions are exemplified as a system of equations, shown in FIG. 5. The core model equations describe the interrelationships between the model variables, including tumor size T, vascular density V, and the drug's PD function and the model parameters that represent the quantitative relations between the processes. Drug concentrations are input into the PD function, which is specific to each drug's MOA.

A NSCLC population model was then created, whose parameters (some of them fixed and others distributed) were estimated using patient data from published clinical trials with cisplatin and pemetrexed, both alone and in combination, as well as distributions of tumor intrinsic growth rate, reported in the literature for untreated NSCLC patients. The population model was used to create disease progression models for a list of cisplatin and pemetrexed treatment protocols.

Then, corresponding modified disease progression models were created. To this end, the NSCLC disease progression model was modified to patients in a training data set of 42 ADC patients who had received C+P as 1st line treatment. The modified model parameters were evaluated using various fitting techniques (e.g. MCMC) until the best fit was obtained ($R^2=0.87$, FIG. 6A), and regression and machine learning methods were applied. Subsequently, the correlating functions between pre-treatment individual medical data of the specific patient and the modified disease progression models were identified, by which a personalized disease progression model (i.e. patient-specific individualized model) is determined.

The inventors have constructed a two-step personalization algorithm, which uses a system model modifier (e.g. based on a Bayesian estimator) to stratify patients and estimate the value of their individual parameter, λ, and further uses a predictor module (e.g. based on a Bayesian predictor) to predict personal dynamic changes in tumor size, based on pretreatment patient data for the specific patient (i.e. medical data of the specific patient). The full personalization algorithm for C+P treatment includes the population model/disease progression model, the modified disease progression model creation using the system model modifier (e.g. using Bayesian estimator), and the personalized disease progression model creation using prediction module/algorithm (e.g. based on Bayesian predictor).

In this example, the above personalization algorithm has been examined using the "leave-one-out" cross validation method. Employing this method, a single patient was excluded from the studied group, and the model was trained as above, on the rest of the group. Subsequently, (i) pretreatment data of the excluded patient were input to create the personalized disease progression model, (ii) this model was simulated to predict personal tumor size changes under treatment, for this patient, (iii) personalized disease progression model predictions were then compared to the clinical tumor measurements (obtained by computer tomography, CT) of that patient, (iv) this procedure was reiterated for all the patients, resulting in an accurate overall prediction of tumor size and response ($R^2=0.67$) as can be seen in FIG. 6B.

FIGS. 6A and 6B illustrate the experimental results showing the fitted vs. observed tumor sizes in all the 42 patients. Each empty circle stands for the value of the predicted tumor size (lesion diameter) in the ordinate, versus the clinically observed tumor size in the abscissa (patients' data from hospitals). The diagonal line marks the identity line. FIG. 6A shows a plot resulting from the personalized model training, indicating the ability of the mathematical model created according to the invention to replicate the recorded data, and FIG. 6B shows a plot resulting from the "leave-one-out" validation of the personalized models. Individual predictions by the personalized model are shown in FIG. 7 showing predicted tumor size dynamics of Patient #11 under the 1st line C+P treatment, using only pretreatment data, i.e. medical data of Patient #11: Line 600 is the mean predicted tumor size, lines 610 and 620 are 50% confidence intervals, as compared to the observed clinical data of tumor sizes, shown on the graph as empty black circles.

In the present example, the creation of the population model and the disease progression models, the modification of the disease progression models and the personalization of the disease progression models were as follows: The population model and disease progression models were created by combining mathematical and statistical components and applying an alternative modeling method. The population model describes NSCLC progression and its response to different therapeutic interventions, as well as evolution of resistance to these therapies. Statistical and mathematical modeling approaches were merged, in order to gain the advantages and compensate for the caveats of each independent approach.

The modeling uses dynamical ODE systems, including a mechanistic description of NSCLC progression, which is based on in-depth understanding of disease biology, and the relevant biological processes including tumor cell proliferation and death, angiogenesis, dormancy, somatic evolution of cancer aggressiveness, development of resistance, etc. The model accounts for the inter-relationships of these processes on different scales, combining cellular components, molecular factors, and signaling proteins together in one system of ODEs.

The disease progression models utilize characteristic profile (consisting of specific distributions, elimination and MOA) of each drug used for the advanced/locally advanced ADC patients. Depending on the drug concentration (evaluated by a PK model) and its MOA (described by a PD model), it affects tumor growth and normal physiology differently. The exemplified system had a library of the relevant treatment protocols (single-drug and combinations) per treatment stage, e.g. cisplatin, carboplatin, pemetrexed, docetaxel, paclitaxel, bevacizumab, erlotinib. Also in this specific but not limiting example, the modeling uses Nonlinear Mixed Effects Modeling (NLMEM) strategy which is suitable for personalized prediction of disease dynamic response to treatment as it accounts for errors in data measurement and accommodates the distribution of biomedical parameters in the patient population. The NLMEM approach captures the variation in tumor dynamics, characterizing NSCLC, and adequately represents specific patients. Multiple alternative modeling was employed for developing the NLMEM models.

A major problem in modeling a biological process is the lack of certitude that the model is both suitable to describe the data complexity (e.g., the evolution of resistance), and, at the same time, not too complex to prevent over-fitting and unidentifiable parameters. Therefore, in contrast to the state-of-the-art approach of "bottom-up" modeling, based on a preconceived underlying mechanism, several plausible models are designed on the basis of both the underlying biological assumptions, and on extensive clinical data, finally selecting the best-performing model, as determined by its ability to retrieve many patients' profiles. Thus, design of several alternative models of NSCLC progression (along the above described lines) was done, and compared for their "goodness-of-fit" to the clinical datasets. The strategy guarantees objective testing of a variety of reasonable models that differ in parsimony and predictive capability. Accordingly, this approach significantly increases the probability that the appropriate model is selected, i.e. a maximally parsimonious and reliable model, which is best suited for entrenching in a clinical prediction algorithm.

The determination of the personalized disease progression models involved a Bayesian estimator that modifies the reference disease progression models and evaluates the personal model parameters based on the pre-treatment patient's data, by using functions constructed from the analysis of the training data. The Bayesian estimator produces a personalized model, based on the population generic NSCLC model, but whose parameters are particularized for the given patient. A Bayesian predictor was used in simulating the personalized disease progression model to predict the patient's short- and long-term effects, as materialized in tumor progression, survival, and response to endpoint(s). The simulation output of the Bayesian predictor was converted by a Report Generator into a descriptive graphical/textual report, providing definitive, clinically critical answers to the prognosis questions (progression-free probability at time X, survival time) and treatment queries (tumor size after a given therapy, response for the specific regimen, time to development of resistance to a drug, etc.). The above algorithms were developed using the training-designated part of the clinical datasets.

For adjustment of the population model to a disease progression model (patient population under a specific treatment), and for the individualization of the algorithm (determining the personalized disease progression models), independent retrospective data was collected from diverse sources. Specifically, information from literature on pathophysiology of ADC/NSCLC progression, PK of relevant chemical and biological drugs, PD effects of these drugs in patients, etc, were collected, and the clinical database of NSCLC patients at hand, as well as additional patients' data, were used.

Thus, the present invention provides a novel technique enabling efficient prediction of a treatment effect on a specific patient, thus allowing selection the most suitable treatment protocol for said patient. The technique of the present invention utilizes medical data of the specific patient and the physician defined endpoint(s) to create a set of personalized disease progression model each being optimized for specific patient's medical data and being based on a dedicated treatment protocol optimized by the training data set.

The invention claimed is:

1. A computerized system for use in planning a medical treatment for an individual having a specific cancer disease, the system comprising:
a data input utility configured for receiving input data comprising first and second input data, the first input data comprising medical data of a specific individual, and the second input data comprising one or more predetermined endpoints defined by a physician as a treatment target with respect to the specific individual, the one or more predetermined endpoints comprising at least one of a time to disease progression or tumor size over time with respect to the cancer disease;
a database including one or more standard disease progression models and training data sets of medical data of a group of individuals that had the specific cancer disease, each of the standard disease progression models including a set of differential equations forming a population model representing a uniform general mechanistic model applicable for all patients;
a data processor comprising a modifier module, a predictor module and a simulator module,
the modifier module being configured to apply machine learning to the one or more standard disease models by utilizing the medical data of a group of individuals that had the specific cancer disease and generate respective one or more modified disease progression models, each modified disease progression model comprising modifications of the standard disease models based on the medical data of the group of individuals and functions describing relations between the medical data of the group of individuals and variations of one or more coefficients of the differential equations in the standard disease progression models, each modified disease progression model defining relationships between tumor size, vascular system, and mechanism of action of one or more drugs included in one or more treatment plans comprising one or more predetermined treatment protocols for treating said specific cancer disease, thereby describing dynamics of the cancer disease, in time, under treatment by the one or more treatment plans;
the predictor module being configured for processing the one or more modified disease progression models by utilizing said first input data and generating respective one or more personalized disease progression models adapted to the individual,
the simulator module being configured for processing said one or more personalized disease progression models with respect to said one or more endpoints, and generating output data indicative of personal treatment effect with respect to said one or more treatment plans and each of said one or more endpoints, the output data comprising recommendation data as to whether use said one or more treatment plans in treating the individual; and a data presentation utility configured for presenting said output data to the physician, thereby enabling evaluation of said one or more treatment plans with respect to each of said one or more endpoints.

2. The computerised system of claim 1, wherein the one or more treatment plans include a plurality of treatment plans and said data processor comprises an analyzer module configured for analyzing said output data and ranking said plurality of treatment plans according to each of said one or more endpoints with respect to the specific individual and said specific cancer disease, and generating, as part of the recommendation data, ranking data indicative of said ranking.

3. The computerized system of claim 1, further comprising a communication utility for communicating with the database for accessing reference data comprising said one or more treatment plans and said one or more standard disease models.

4. The computerized system of claim 1, wherein said standard disease model comprises data indicative of disease progression for untreated population, pharmacokinetics (PK) and pharmacodynamics (PD) of drugs used in said one or more treatment plans, and response to treatment for treated population.

5. The computerized system of claim 1, wherein said medical data comprise data indicative of at least one of the following: past medical data; physical examination; pathology review; histologic subtype; imaging data; blood counts (cbc);

biochemistry profile; hormone profile and markers of inflammation; tumor markers; molecular diagnostic tests; immunohistochemical staining (ihc); gene status, mutation in one or more genes, one or more amplification in one or more copies, genetic recombination, partial or complete genetic sequencing.

6. The computerized system of claim 5, wherein said medical data further comprises at least one of the following: an inter-dosing interval, drug dose, pharmacokinetics (PK) and pharmacodynamics (PD) information of one or more treatment regimens, each comprising at least one of chemotherapy drug, immunotherapy drug, or biological drug.

7. The computerized system of claim 5, wherein said imaging data comprise images at different times of a body part or organ.

8. The computerized system of claim 1, wherein said one or more endpoints comprise at least one of the following: survival, growth arrest of tumor, or time profile of the individual's reaction to one or more selected drugs.

9. A method for use in planning a medical treatment for an individual under specific cancer disease, the method comprising:

providing first input data comprising medical data of a specific individual, and second input data comprising data indicative of one or more endpoints defined by a physician as treatment target(s) with respect to the specific individual, said one or more endpoints comprising at least one of time disease progression or tumor size over time with respect to the cancer disease;

providing reference data indicative of one or more predetermined treatment plans each comprising one or more treatment protocols for treating said specific cancer disease;

providing one or more standard disease progression models and training data sets of medical data of a group of individuals that had the specific cancer disease, each of the standard disease progression models including a set of differential equations forming a population model representing a uniform general mechanistic model applicable for all patients;

providing one or more modified disease progression models generated by applying machine learning to the one or more standard disease models by utilizing the medical data of a group of individuals that had the specific cancer disease, each modified disease progression model comprising modifications of the standard disease models based on the medical data of the group of individuals and functions describing relations between the medical data of the group of individuals and variations of one or more coefficients of the differential equations in the standard disease progression models, each modified disease progression model defining relationships between tumor size, vascular system, and mechanism of action of one or more drugs included in each of the one or more treatment plans, hereby describing dynamics, in time, of said specific cancer disease under treatment by said one or more treatment plans;

processing said one or more modified disease progression models by utilizing said first and second input data, and generating respective one or more personalized disease progression models being adapted to the specific individual; and processing the one or more personalized disease progression models and generating output data indicative of a personal treatment effect with respect to each of said one or more treatment plans and said one or more endpoints, the output data comprising recommendation data as to whether use said one or more treatment plans in treating the individual, thereby enabling selection of the treatment plan for the specific patient and specific cancer disease.

10. The method of claim 9, further comprising analyzing said output data and ranking said one or more treatment plans according to each of said one or more endpoints with respect to the specific individual and said specific cancer disease, and generating, as part of the recommendation data, ranking data indicative of said ranking, enabling said selection of the treatment plan for the specific patient and specific cancer disease.

11. The method of claim 9, comprising obtaining from the database said standard disease models.

12. The method of claim 9, wherein said standard disease model comprises data indicative of disease progression for untreated population, pharmacokinetics and pharmacodynamics of drugs used in said one or more treatment plans, and response to treatment for treated population.

13. The method of claim 9, wherein said medical data comprises data indicative of at least one of the following: past medical data; physical examination; pathology review; histologic subtype; imaging data; blood counts (cbc);

biochemistry profile; hormone profile and markers of inflammation; tumor markers; molecular diagnostic tests; immunohistochemical staining (ihc); gene status, mutation in one or more genes, one or more amplification in one or more gene copies, genetic recombination, partial or complete genetic sequencing, death indicator.

14. The method of claim 9, wherein said medical data further comprises at least one of the following: inter-dosing interval, drug dose, [pharmacokinetics (PK) and pharmacodynamics (PD) information of one or more treatment regimens, each comprising at least one chemotherapy, immunotherapy, or biological drug.

15. The method of claim 9, wherein said imaging data comprise images at different times of a body part or organ.

16. The method of claim 9, wherein said one or more endpoints comprise at least one of the following: survival, growth arrest of tumor, or time profile of the individual's reaction to one or more selected drugs.

17. The method of claim 9, further comprising utilizing the output data to treat the individual.

\* \* \* \* \*